US010004577B2

(12) United States Patent
Richard (10) Patent No.: US 10,004,577 B2
(45) Date of Patent: Jun. 26, 2018

(54) TRANSFIXED MULTIPLE DENTAL PROSTHESIS

(71) Applicant: ANTHOGYR, Sallanches (FR)

(72) Inventor: Hervé Richard, Notre Dame de Bellecombe (FR)

(73) Assignee: ANTHOGYR, Sallanches (FR)

( * ) Notice: Subject to any disclaimer, the term of this patent is extended or adjusted under 35 U.S.C. 154(b) by 149 days.

(21) Appl. No.: 15/066,269

(22) Filed: Mar. 10, 2016

(65) Prior Publication Data

US 2016/0270888 A1 Sep. 22, 2016

(30) Foreign Application Priority Data

Mar. 17, 2015 (FR) ..................................... 15 52207
Jul. 3, 2015 (FR) ..................................... 15 56340

(51) Int. Cl.
*A61C 8/00* (2006.01)

(52) U.S. Cl.
CPC .......... *A61C 8/0068* (2013.01); *A61C 8/0022* (2013.01); *A61C 8/0048* (2013.01); *A61C 8/0069* (2013.01); *A61C 8/0075* (2013.01)

(58) Field of Classification Search
CPC ... A61C 8/0048; A61C 8/0059; A61C 8/0069; A61C 8/0056; A61C 8/0066; A61C 8/0072; A61C 8/0074; A61C 8/0071; A61C 8/0095; A61C 8/004; A61C 13/0019

See application file for complete search history.

(56) References Cited

U.S. PATENT DOCUMENTS

| 5,221,205 A * | 6/1993 | Kuch ................... A61C 8/0048 433/181 |
| 5,238,405 A * | 8/1993 | Marlin ................. A61C 8/0048 433/172 |
| 5,556,280 A * | 9/1996 | Pelak .................. A61C 8/0048 433/172 |
| 5,733,124 A * | 3/1998 | Kwan .................. A61C 8/0001 433/173 |
| 6,068,479 A * | 5/2000 | Kwan .................. A61C 8/0001 433/173 |
| 6,663,388 B1 | 12/2003 | Schar |
| 8,727,774 B1 | 5/2014 | Arendt |

(Continued)

FOREIGN PATENT DOCUMENTS

| EP | 2223667 A1 | 9/2010 |
| KR | 101307411 B1 | 9/2013 |
| WO | 2006033098 A1 | 3/2006 |

*Primary Examiner* — Nicholas Lucchesi
(74) *Attorney, Agent, or Firm* — William H. Eilberg (57) ABSTRACT

Transfixed multiple dental prosthesis intended to be attached and fixed to a plurality of dental implants by several transfixing screws, each having a shank with a threaded portion intended to be received by screwing in a respective dental implant. Each transfixing screw is held captive in a respective bore formed in the transfixed multiple dental prosthesis and extending along a respective axial direction. Each transfixing screw is movable in rotation about the axial direction of the respective bore and is movable in translation along the axial direction of the respective bore between a retracted position and at least one screwing position. In the retracted position, the threading of the threaded portion of the transfixing screw does not protrude from the bore.

16 Claims, 11 Drawing Sheets

(56) References Cited

U.S. PATENT DOCUMENTS

| | | | |
|---|---|---|---|
| 2003/0149485 A1* | 8/2003 | Tornier | A61F 2/30721 623/18.11 |
| 2007/0259315 A1 | 11/2007 | Last-Pollak | |
| 2011/0318706 A1 | 12/2011 | Brajnovic | |
| 2012/0156645 A1* | 6/2012 | Jacoby | A61C 8/0062 433/173 |
| 2013/0266913 A1 | 10/2013 | Brajnovic | |
| 2014/0178839 A1* | 6/2014 | Berger | A61C 13/2255 433/173 |
| 2015/0064653 A1* | 3/2015 | Grobbee | A61C 13/2656 433/199.1 |
| 2015/0230891 A1* | 8/2015 | Grobbee | A61C 8/0048 433/199.1 |

* cited by examiner

TRANSFIXED MULTIPLE DENTAL PROSTHESIS

TECHNICAL FIELD OF THE INVENTION

The present invention relates to the field of dental implantology, in particular the treatment of loss of teeth from the dental arch using a multiple prosthesis of the transfixed type, which is intended to be attached and fixed to a plurality of dental implants.

A multiple prosthesis of the transfixed type, supported on implants, is intended to rest on the dental arch of the patient by being fixed to several dental implants that are implanted in the maxillary or mandibular bone of the patient, in order to form several prosthetic teeth. The prosthesis is fixed to the implants by fixing screws that pass through the prosthesis and that each penetrate a respective implant, hence the expressions "transfixed prosthesis" and "transfixing screw". The prosthesis must be able to be removed if necessary, for example for repair.

For reasons relating to mechanical stability, especially relating to the hold of the implant in the maxillary or mandibular bone, the implants are oriented in axial directions which are oblique in relation to each other and which are generally oblique with respect to the general surface of the dental arch.

On account of the oblique orientations of the implants relative to each other, angled abutments are often used. An angled abutment is an intermediate component intended to be attached to the implant in a first axial direction (corresponding to the longitudinal direction of the implant), having an internally threaded cavity and oriented in a second axial direction forming an angle with the first axial direction. The internally threaded cavity receives the transfixing screw in the second axial direction. The use of abutments increases the number of components to be manipulated by the practitioner and greatly complicates his task, since the abutments need to have precise heights, angles and orientations.

Moreover, to ensure that a transfixed multiple dental prosthesis is fitted correctly in the mouth, and to allow the practitioner to check its suitability before fixing it, it is necessary to start with a step in which the dental prosthesis is placed on the dental arch of the patient. During this placement, the patient opens his mouth as far as possible in order to allow the practitioner to insert the transfixed multiple dental prosthesis by translation into his mouth until it is placed on the dental arch of the patient. The practitioner then has to insert the different transfixing screws into bores that are formed in the dental prosthesis. However, the transfixing screws have very small dimensions, which make them difficult to manipulate. There is therefore a risk of a screw escaping the practitioner and falling into the patient's mouth, with the possibility of the patient swallowing it. This is the case, for example, in the document EP 2 223 667 A1, which describes a transfixed multiple dental prosthesis according to the preamble of claim 1.

To limit the risks posed by the manipulations of the transfixing screws, the applicant has conceived of the transfixing screws being rendered captive in the bores formed in the dental prosthesis. The transfixing screws are then rigidly connected to the dental prosthesis before the dental prosthesis is introduced into the patient's mouth. In this case, the threaded shank of the transfixing screw protrudes at least in part and permanently below the dental prosthesis, from the bore in which the transfixing screw is inserted. This permanent protrusion, combined with the limited extent to which the patient's mouth can be opened, poses a high risk of conflict between the threaded shank of the screws and the dental implants, when the practitioner introduces the transfixed multiple dental prosthesis, by translation, into the patient's mouth with a view to placing it on the dental arch of the patient. However, in the event of conflict (by a threaded shank of a screw abutting against an implant), there is a risk of the threading of the transfixing screw (of very small dimensions) being damaged. A damaged transfixing screw can no longer be screwed into the dental implant situated in line with it, or it may be screwed incorrectly into the dental implant. The damaged transfixing screw may even sometimes break while being screwed into the dental implant, or it may damage the internally threaded portion of the dental implant receiving it, which is traumatic since said dental implant is already osseointegrated, and its withdrawal, in order to remove the broken threaded portion of the transfixing screw or to change the dental implant, is barely conceivable.

The document U.S. Pat. No. 6,663,388 B1 relates exclusively to a one-piece dental prosthesis and more particularly describes the fixation of a dental abutment on a dental implant by means of a fixing screw that is held captive in a bore of said dental abutment. The fixing screw protrudes permanently from the bore of the dental abutment.

SUMMARY CF THE INVENTION

A problem addressed by the present invention is to permit optimal and removable fixation of a transfixed multiple dental prosthesis, supported on implants, with the aid of means of connection to the implants that limit the risks of the manipulation by the practitioner and that limit the risks of damage.

To achieve these objects and others, the invention proposes a transfixed multiple dental prosthesis intended to be attached and fixed to a plurality of dental implants by means of several transfixing screws, each having a shank with a threaded portion intended to be received by screwing in a respective dental implant; according to the invention:

each transfixing screw is held captive in a respective bore formed in the transfixed multiple dental prosthesis and extending along a respective axial direction, each captive transfixing screw is movable in rotation about the axial direction of the respective bore and is movable in translation along the axial direction of the respective bore between a retracted position and at least one screwing position, in the retracted position, the threading of the threaded portion of the transfixing screw does not protrude from the respective bore in which the transfixing screw is held captive, in the screwing position, the threading of the threaded portion of the transfixing screw protrudes at least in part from the respective bore in which the transfixing screw is held captive.

If, during the introduction of the transfixed multiple dental prosthesis into the patient's mouth, a transfixing screw comes into conflict with an obstacle formed by a dental implant (or an adjacent tooth of the patient), it can move to the retracted position in order to escape the obstacle. In practice, if the practitioner senses a slight resistance during the introduction of the transfixed multiple dental prosthesis into the patient's mouth, which is a sign of probable conflict between a transfixing screw and an obstacle formed by a dental implant (or an adjacent tooth), a gentle reciprocating translation movement of low amplitude, toward and away from the maxillary or mandibular bone, is sufficient to cause the movement of the transfixing screw to the retracted position, such that the obstacle is then overcome. The practitioner can then continue the introduction of the transfixed multiple dental prosthesis into the patient's mouth, until it is placed on the dental arch of the patient.

Advantageously, provision can be made that:
the shank of each transfixing screw terminates in a distal centering portion following on from the threaded portion,
the distal centering portion has a cross section whose dimensions decrease in the direction away from the threaded portion,
in the retracted position, the transfixing screw protrudes from the bore, in which it is held captive, via all or part of its centering portion.

When bearing laterally on an obstacle, the shape of such a centering portion causes the appearance of a force that tends to move the transfixing screw toward its retracted position. Moreover, such centering portion makes it possible to properly center the transfixing screw with respect to the dental implant in order to promote correct screwing in the latter.

Preferably, the centering portion can be substantially conical or frustoconical.

Advantageously, provision can be made that:
the threading of the threaded portion of the transfixing screw has a first threading portion, and it has a second threading portion following on from the first threading portion and extending as far as the centering portion,
the first threading portion has a constant external diameter,
the second threading portion has an external diameter which decreases in the direction of the centering portion.

The second threading portion, with its external diameter which decreases in the direction of the centering portion, engages more progressively in the internally threaded portion of the implant situated in line with it.

Preferably, the threading of the threaded portion of the transfixing screw can have at least two threads, preferably three threads. The practitioner will thus have to apply fewer screwing turns to the screw to ensure that the latter engages in the dental implant by being retained there by a retention force of satisfactory value. Moreover, the course of screwing of the transfixing screw is also reduced further such that it engages in the dental implant by being retained there by a retention force of satisfactory value, which makes it possible to further limit the axial size of the transfixing screw and contributes to facilitating the introduction of the dental prosthesis into the patient's mouth.

In a first particular embodiment of the invention, provision, can advantageously be made that:
the transfixing screw has a portion with a radial widening, from which there extends a transfixing screw portion that has an external cross section with dimensions smaller than those of the radial widening,
each transfixing screw is held captive in its respective bore by way of a fixing member which simultaneously:
engages at least in part in an inner peripheral seat formed in the respective bore of the transfixed multiple dental prosthesis,
has, under the radial widening and around the transfixing screw portion, an external cross section with dimensions smaller than those of the radial widening.

The screw thus has a very simple shape, allowing it to be produced at low cost.

In this first particular embodiment of the invention, the translation of the transfixing screw between its retraction and screwing positions can be made possible by the fact that the inner peripheral seat formed in the respective bore, and/or the transfixing screw portion having an external cross section with dimensions smaller than those of the radial widening, have a height in the axial direction greater than the height of the part of the fixing member engaging in the inner peripheral seat.

In a first variant of the first particular embodiment of the invention, provision can be made that:
the fixing member is a retaining ring with a radial slit,
the inner peripheral seat is an annular groove extending radially with respect to the axial direction of the bore.

In a second variant of the first particular embodiment of the invention, provision can be made that:
the fixing member comprises an annular ring which has symmetry of revolution about a central axis and which extends along the central axis between a proximal end and a distal end,
the fixing member comprises at least one angular portion developing in an arc between a first end, joined to the distal end of the annular ring, and a second free end,
said at least one angular portion is in part movable from its first end, in a transverse plane perpendicular to the central axis, between a retracted position and at least one protruding position, being elastically returned permanently to the protruding position,
in the retracted position, said at least one angular portion is included within the volume of a cylinder continuing the outer cylindrical surface of the annular ring,
in the protruding position, the second free end of said at least one angular portion extends beyond the volume of the cylinder continuing the outer cylindrical surface of the annular ring.

In the second variant of the first particular embodiment of the invention, provision can advantageously be made that the inner peripheral seat has at least one angular groove portion extending radially with respect to the axial direction of the bore. An inner peripheral seat of this kind is particularly useful when the space available radially in the dental prosthesis for producing the inner peripheral seat is limited in certain radial directions.

Alternatively, the inner peripheral seat can be an annular groove extending radially with respect to the axial direction of the bore.

In a second particular embodiment of the invention, provision can advantageously be made that the transfixing screw is mounted rotatably and retained in translation in its respective bore by way of a compressible retaining ring, preferably by means of a radial slit, simultaneously engaging in an outer peripheral groove formed on the transfixing screw and in an inner peripheral groove formed in the respective bore.

In this second particular embodiment of the invention, the translation of the transfixing screw between its retracted and screwing positions can be made possible by the fact that the inner peripheral groove formed in the respective bore, and/or the outer peripheral groove formed on the transfixing screw, have a height, in the axial direction, greater than the height of the retaining ring engaging in the inner peripheral groove formed in the respective bore.

According to another aspect of the invention, a dental implant is proposed extending between a distal connection end, intended to receive a transfixed multiple dental prosthesis, and a proximal anchoring end, intended to be inserted in the maxillary or mandibular bone of a patient, comprising a blind inner bore that leads to the distal connection end, and comprising a first internally threaded portion intended to receive the threaded portion of a transfixing screw; according to the invention, the first internally threaded portion extends from the orifice of the blind inner bore in the direction of the proximal anchoring end.

Such a dental implant, in combination with a transfixed multiple dental prosthesis as described above, forms a dental assembly.

Since the first internally threaded portion extends from the orifice of the blind inner bore in the direction of the proximal anchoring end, the total length of the implant can be reduced such that it protrudes to a lesser extent when it is inserted into the maxillary or mandibular bone of a patient. This effectively limits the risks of conflict with the transfixing screws of a transfixed dental prosthesis, and more particularly a transfixed multiple dental prosthesis. Moreover, the total length of the transfixing screw of the dental prosthesis can also be reduced, since it does not need to have such a great length in order to be received by screwing in the dental implant, which further limits the risks of conflict and of damage.

Advantageously, the dental implant can have a screwing socket with a non-circular cross section, accessible from the orifice of the blind inner bore via the first internally threaded portion.

Preferably, the dental implant can have second internally threaded portion, accessible from the orifice of the blind inner bore via the first internally threaded portion and the screwing socket, and having a threading diameter smaller than the threading diameter of the first internally threaded portion. This second internally threaded portion can receive a screw for fixing another dental prosthesis, either multiple or single, or even a dental abutment. The dental implant can thus be suitable for several uses, which limits the number of implants that the practitioner needs to have in stock.

BRIEF DESCRIPTION OF THE DRAWINGS

Other subjects, features and advantages of the present invention will become clear from the following description of particular embodiments, with reference being made to the attached figures in which.

DESCRIPTION OF THE PREFERRED EMBODIMENTS

Figure 1:
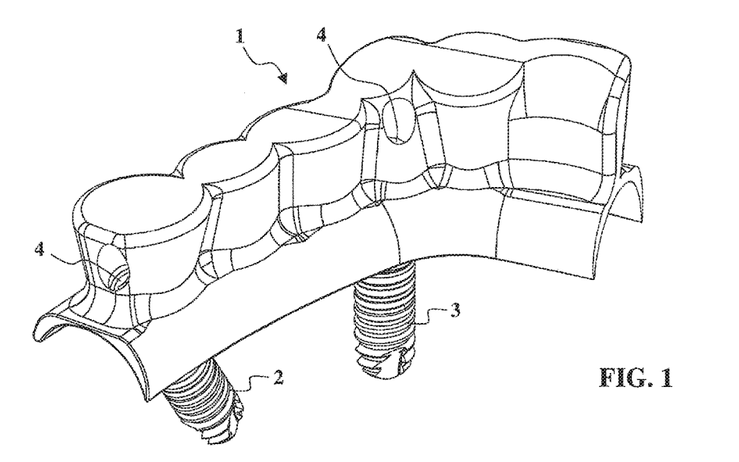
FIG. 1 is a perspective view of a first embodiment of a transfixed multiple dental prosthesis attached and fixed to a plurality of dental implants.
Figure 2:
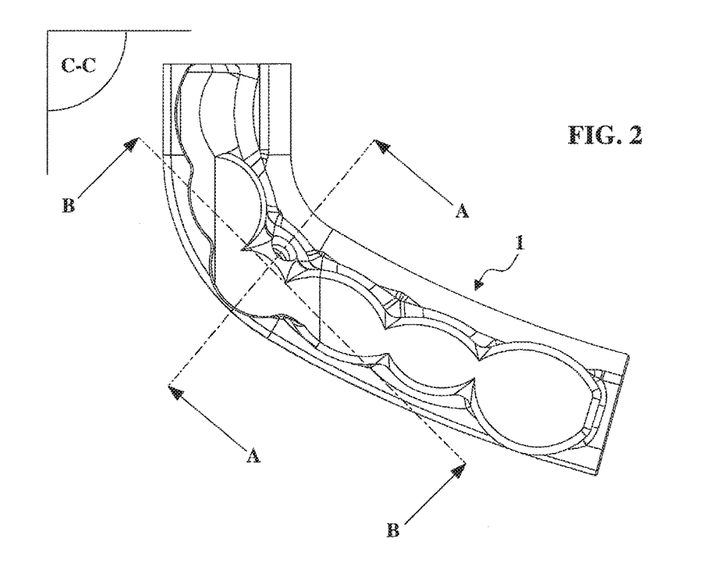
FIG. 2 is a top view of the transfixed multiple dental prosthesis of FIG. 1.

FIGS. 1 and 2 depict a transfixed multiple dental prosthesis 1 intended to be attached and fixed to dental implants 2 and 3 by means of several transfixing screws 4. The dental implants 2 and 3 are oriented obliquely with respect to each other.

Figure 11:
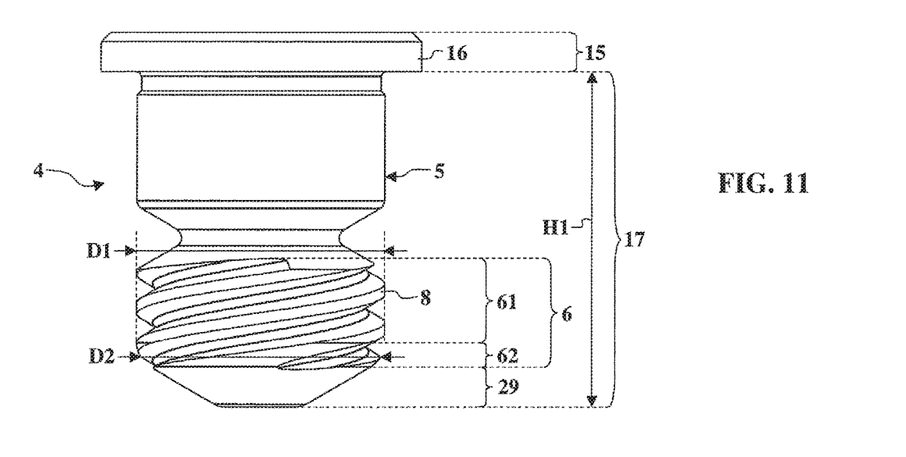
FIG. 11 is a side view of a transfixing screw used in the first embodiment of a transfixed multiple dental prosthesis.
Figure 12:
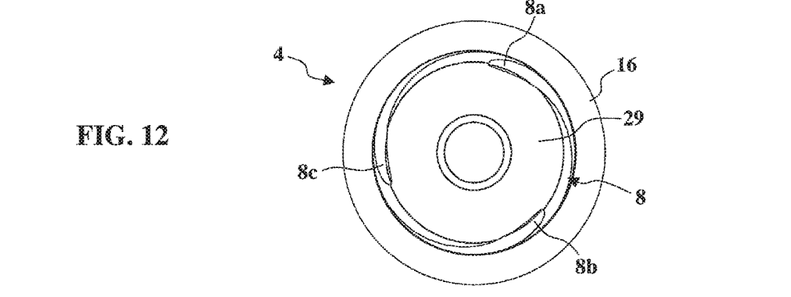
FIG. 12 is a bottom view of the transfixing screw of FIG. 11.

A first embodiment of a dental prosthesis 1 is illustrated in FIGS. 3, 4, 6 and 7. In this embodiment, use is made of a transfixing screw 4 as illustrated in FIGS. 11 and 12. This transfixing screw 4 has a shank 5 with a threaded portion 6 intended to be received by screwing in a dental implant 2 or 3 as illustrated in greater detail in FIG. 5.

Figure 3:
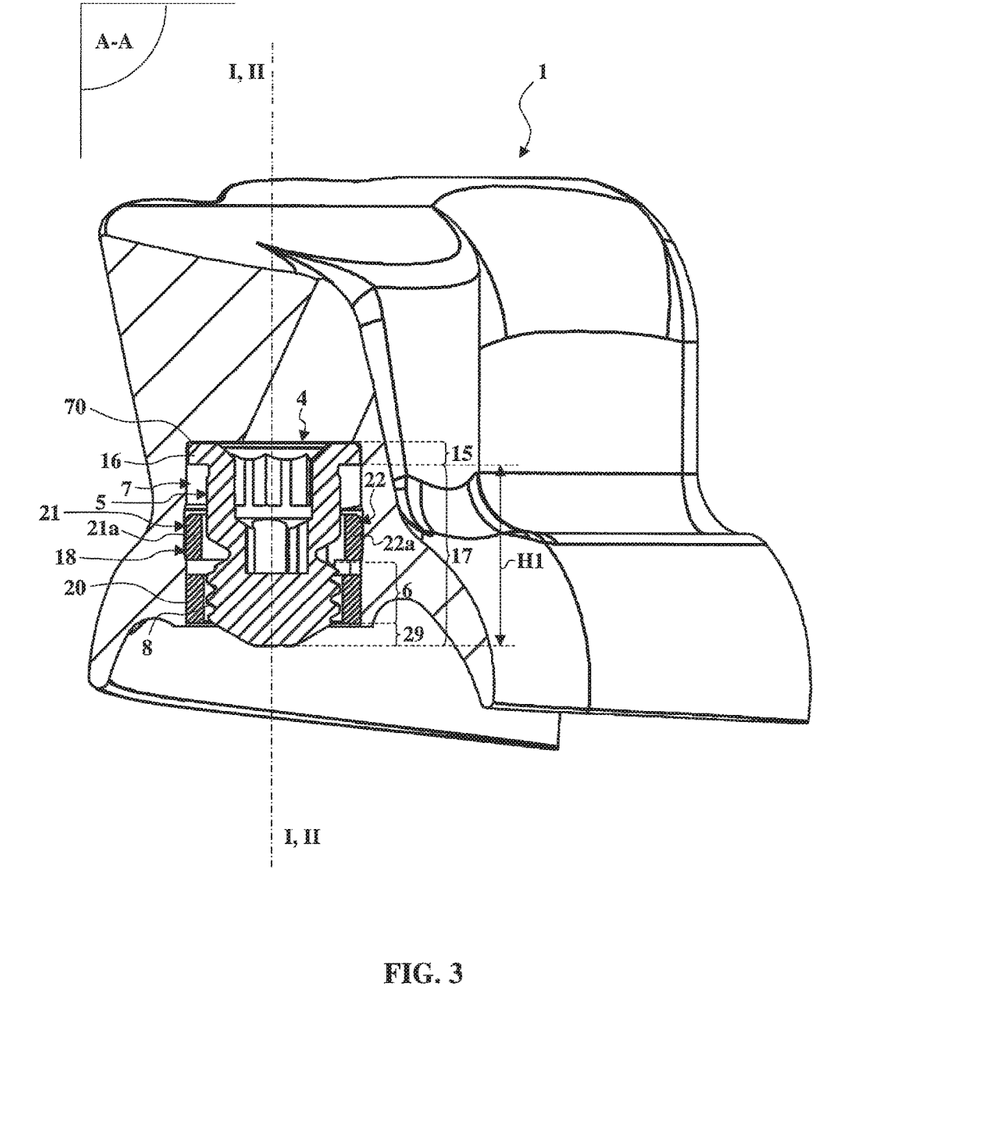
FIG. 3 is a sectional view of the transfixed multiple dental prosthesis of FIG. 1, on a section plane A-A illustrated in FIG. 2.
Figure 4:
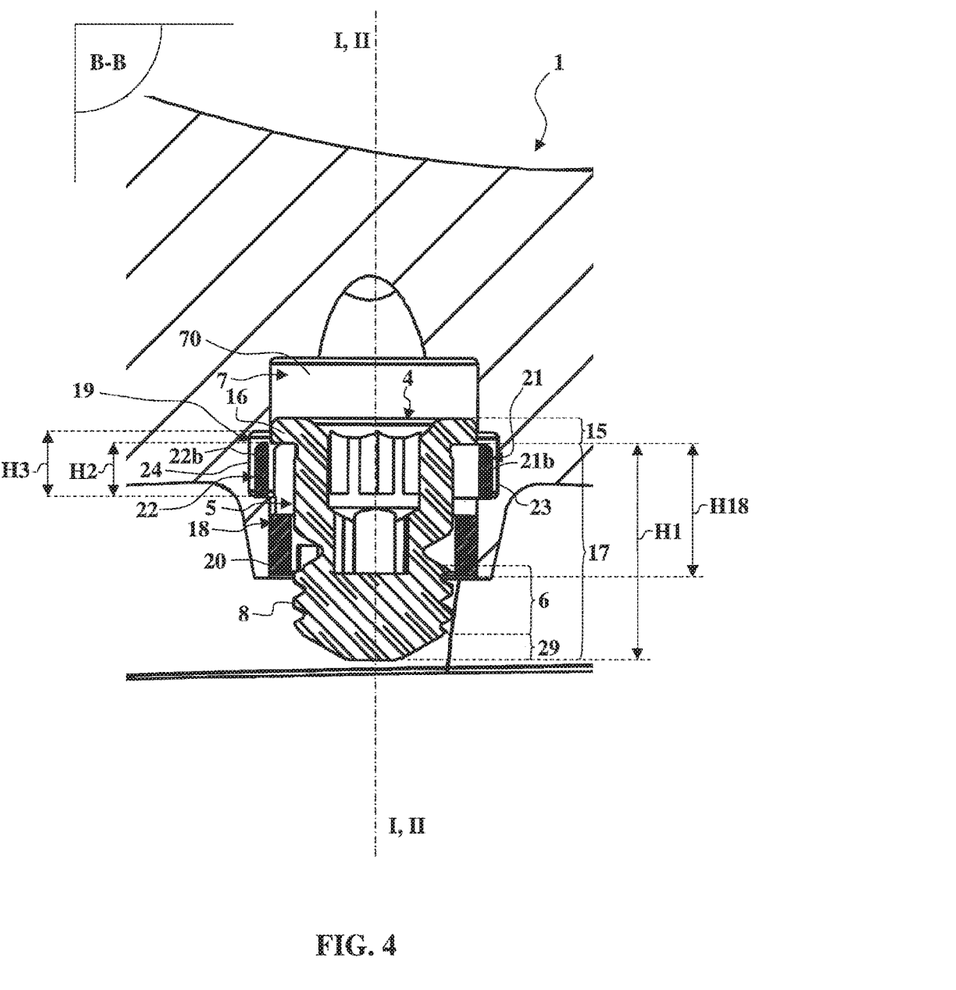
FIG. 4 is a sectional view of the transfixed multiple dental prosthesis of FIG. 1, on a section plane B-B illustrated in FIG. 2.

It will be seen in FIGS. 3 and 4 that the transfixing screw 4 is held captive in a bore 7 formed in the transfixed multiple dental prosthesis 1 and extending in an axial direction I-I. The transfixing screw 4 is movable in rotation about the axial direction I-I and is movable in translation along the axial direction I-I between a retracted position (FIG. 3) and at least one screwing position (FIG. 4).

In the retracted position (FIG. 3), the threading 8 of the threaded portion 6 of the transfixing screw 4 does not protrude from the bore 7 in which the transfixing screw 4 is retained.

In the screwing position (FIG. 4), the threading 8 of the threaded portion 6 of the transfixing screw 4 protrudes at least in part from the respective bore 7 in which the transfixing screw 4 is held captive. This protrusion of the threading 8 from the bore 7 allows the transfixing screw 4 to be received in the dental implant 2 or 3 illustrated in FIG. 5.

Figures 5, 6:
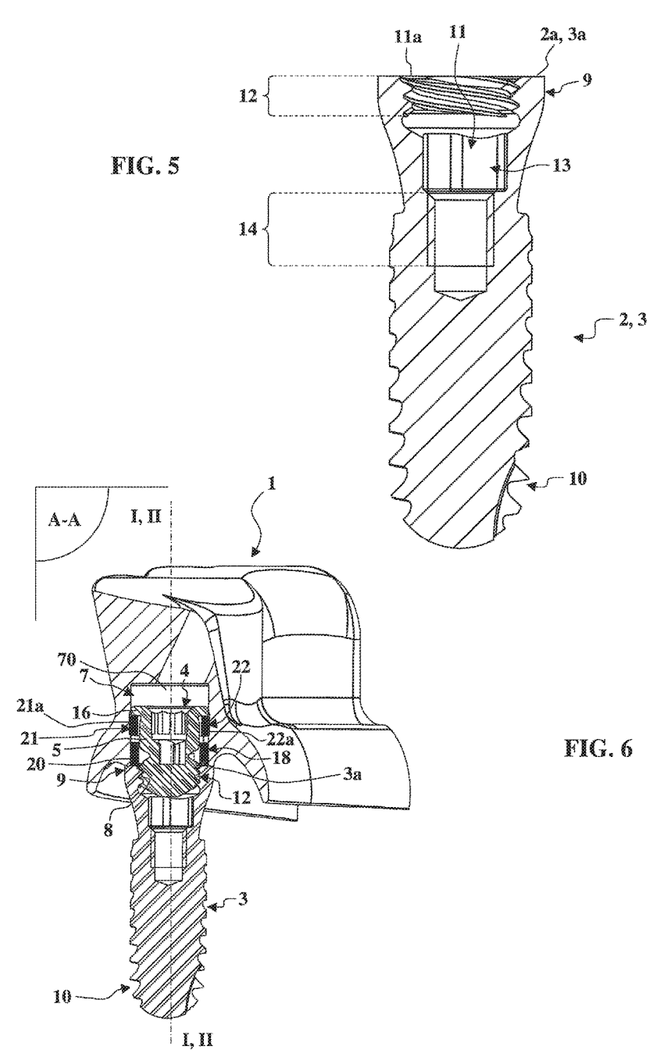
FIG. 5 is a sectional view of a first variant of a dental implant intended to receive the transfixed multiple dental prosthesis of FIG. 1.
FIG. 6 is a sectional view of the transfixed multiple dental prosthesis of FIG. 1, on a section plane A-A illustrated in FIG. 2, attached and fixed to the implant of FIG. 5.

Said dental implant 2 or 3 extends between a distal connection end 9, intended to receive the transfixed multiple dental prosthesis 1, and a proximal anchoring end 10, intended to be inserted (by screwing or impaction) in the maxillary or mandibular bone of a patient. The dental implant 2 or 3 comprises a blind inner bore 11 that leads to the distal connection end 9, and comprising a first internally threaded portion 12 intended to receive the threaded portion 6 of the transfixing screw 4. The first internally threaded portion 12 extends from the orifice ala of the blind inner bore 11 in the direction of the proximal anchoring end 10. The dental implant 2 or 3 also has a screwing socket 13 with a non-circular (for example polygonal) cross section, accessible from the orifice 11e of the blind inner bore 11 via the first internally threaded portion 12. The dental implant 2 or 3 also has a second internally threaded portion 14, accessible from the orifice 11e of the blind inner bore 11 via the first internally threaded portion 12 and the screwing socket 13. The second portion 14 has a threading diameter smaller than the threading diameter of the first internally threaded portion 12 so as to receive a fixing screw or transfixing screw different than the transfixing screw 4 illustrated in FIGS. 11 and 12, for the fixation (directly or by way of a dental abutment) of a single or multiple dental prosthesis, which may or may not be transfixed.

It will be seen from FIGS. 11 and 12 that the transfixing screw has a portion 15 with a radial widening 16, from which there extends a transfixing screw portion 17 that has an external cross section with dimensions smaller than those of the radial widening. It will be seen from FIGS. 3 and 4 that the transfixing screw 4 is held captive in the bore 7 by way of a fixing member 18 which simultaneously:

engages at least in part in an inner peripheral seat formed in the bore 7 of the transfixed multiple dental prosthesis 1, has, under the radial widening 16 and around the transfixing screw portion 17, an external cross section with dimensions smaller than those of the radial widening 16.

To allow the movement of the transfixing screw between its retracted and screwing positions, the transfixing screw portion 17 has a height H1 in the axial direction I-I greater than the height H2 of the part of the fixing member 18 engaging in the inner peripheral seat 19 (FIG. 4). Here, the height H1 is greater than the total height H18 of the fixing member 18.

Alternatively or in addition, the inner peripheral seat 19 can have, in the axial direction I-I, a height H3 greater than the height H2.

The bore 7 has a clearance portion 70 that is able to receive at least part of the transfixing screw 4 in the retracted position.

Figure 8:
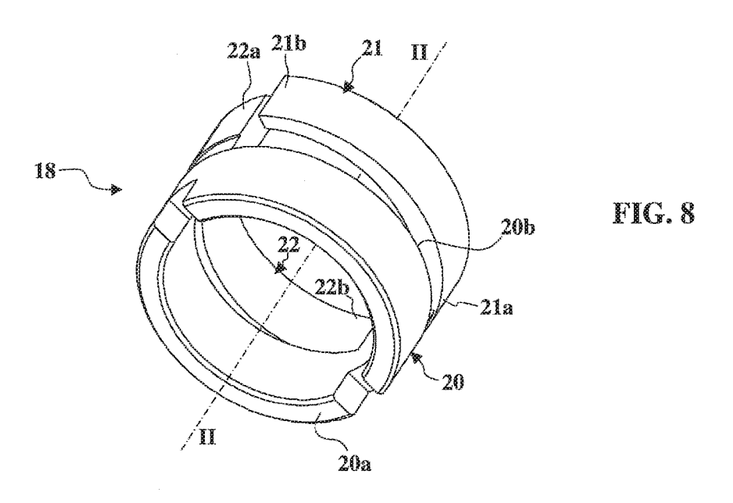
FIG. 8 is a perspective view of a fixing member used in the first embodiment of a transfixed multiple dental prosthesis.
Figure 9:
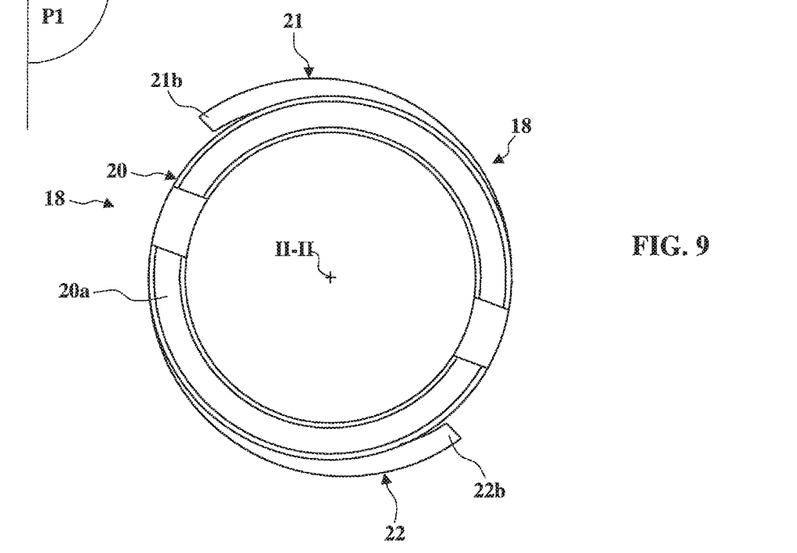
FIG. 9 is a bottom view of the fixing member of FIG. 8.
Figure 10:
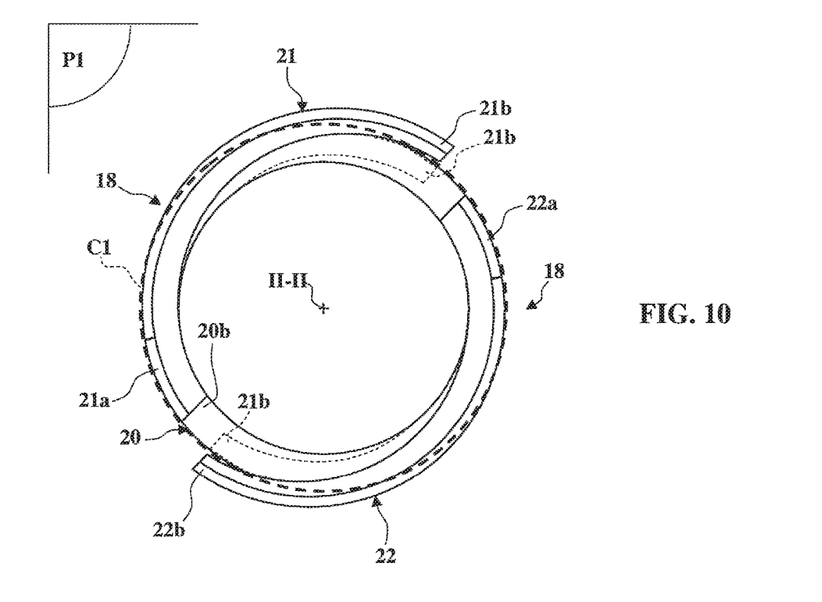
FIG. 10 is a top view of the fixing member of FIG. 8.

The fixing member 18 used in FIGS. 3 and 4 is illustrated in greater detail in FIGS. 8 to 10. In these figures, the fixing member 18 comprises an annular ring 20 which has symmetry of revolution about a central axis II-II and which extends along the central axis II-II between a proximal end 20a and a distal end 20b. The fixing member 18 comprises two angular portions 21 and 22 developing in an arc between a first end 21a or 22a, joined to the distal end 20b of the annular ring 20, and a second free end 21b or 22b. The angular portions 21 and 22 are in part movable from their first ends 21a or 22a, in a transverse plane P1 perpendicular to the central axis II-II, between a retracted position and at least one protruding position, being elastically returned permanently to the protruding position. The retracted position is illustrated by broken lines in FIG. 10, while the protruding position is illustrated by continuous lines in FIG. 10.

In the retracted position, the angular portions 21 and 22 are included within the volume of a cylinder C1 continuing the outer cylindrical surface of the annular ring 20. In the protruding position, the second free ends 21b and 22b of the angular portions 21 and 22 extend radially beyond the volume of the cylinder C1 continuing the outer cylindrical surface of the annular ring 20.

Figure 7:
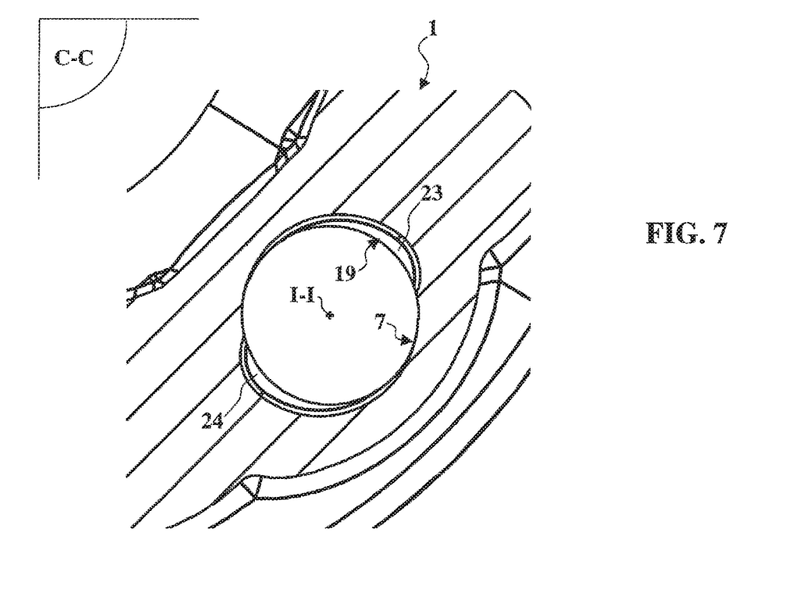
FIG. 7 is a sectional view of the transfixed multiple dental prosthesis of FIG. 1, on a section plane C-C perpendicular to the section planes A-A and B-B illustrated in FIG. 2.

The angular portions 21 and 22 of the fixing member 18 are intended to be received in an inner peripheral seat 19 as illustrated in FIG. 7, which is a sectional view of the transfixed multiple dental prosthesis 1 on a section plane C-C perpendicular to the section planes A-A and B-B illustrated in FIG. 2.

It will be seen from FIG. 7 that the inner peripheral seat 19 has two angular groove portions 23 and 24 extending radially with respect to the axial direction I-I of the bore 7. As is illustrated in FIG. 4, the angular groove portions 23 and 24 receive the angular portions 21 and 22, respectively, in order to retain the fixing member 18 in the bore 7.

Alternatively, the peripheral seat 19 intended to receive the fixing member 18 illustrated in FIGS. 8 to 10 can be an annular groove extending radially with respect to the axial direction I-I of the bore 7.

Figure 13:
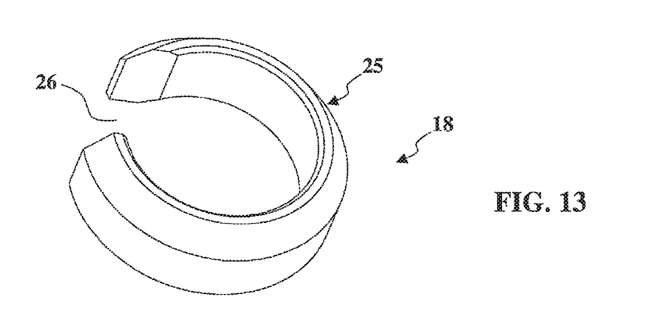
FIG. 13 is a perspective view of a fixing member used in a second embodiment of a transfixed multiple dental prosthesis.

Instead and in place of the fixing member 18 illustrated in FIGS. 8 to 10, the transfixing screw 4 can be held captive in the bore 7 by way of a fixing member 18 as illustrated in FIG. 13, which is a retaining ring 25 that is rendered elastically compressible by means of a radial slit 26.

In the case where the fixing member as illustrated in FIG. 13 is used, the inner peripheral seat 19 for its part is in the form of an annular groove extending radially with respect to the axial direction I-I of the bore 7.

In a second embodiment of the transfixed multiple dental prosthesis 1, as illustrated in FIGS. 14 to 19, the transfixing screw 4 can be mounted rotatably and retained in translation in the bore 7 by way of a compressible retaining ring 25 as illustrated in FIG. 13. The retaining ring 25 is in this case rendered radially compressible by means of a radial slit 26.

In FIGS. 14 to 19, the retaining ring 25 simultaneously engages in an outer peripheral groove 27 formed on the transfixing screw 4 and in an inner peripheral groove 28 formed in the bore 7.

Figure 14:
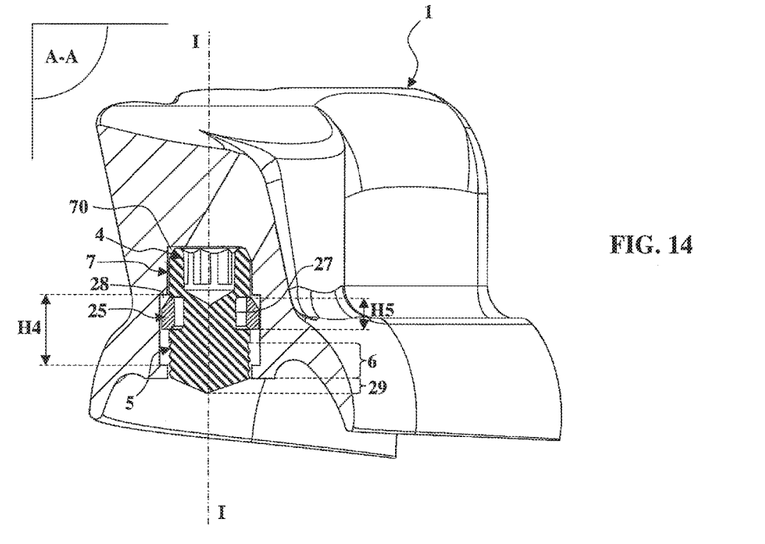
FIGS. 14 and 15 are sectional views of a first variant of the second embodiment of a transfixed multiple dental prosthesis.
Figure 15:
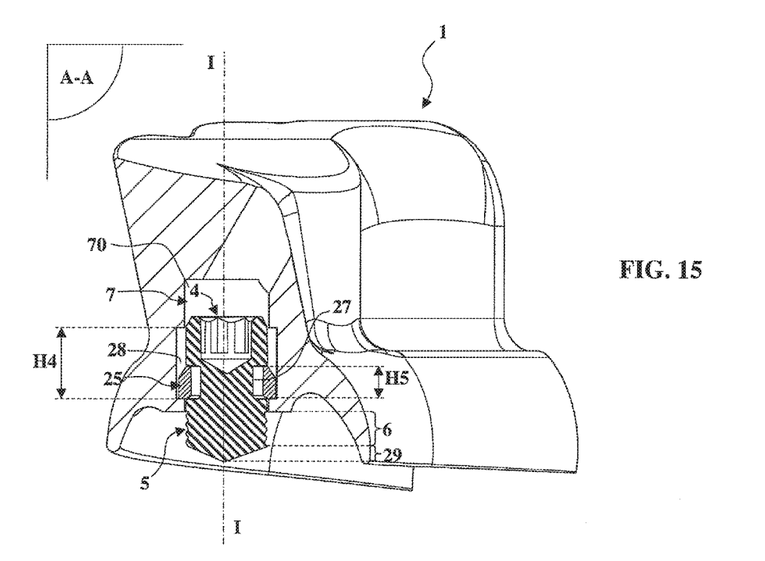

In the first variant illustrated in FIGS. 14 and 15, the translational ability of the transfixing screw 4 to move between its retracted and screwing positions is permitted by the fact that the inner peripheral groove 28 formed in the bore 7 has a height H4, in the axial direction I-I, greater than the height H5 of the retaining ring 25 engaging in the inner peripheral groove 28 formed in the bore 7.

Figure 16:
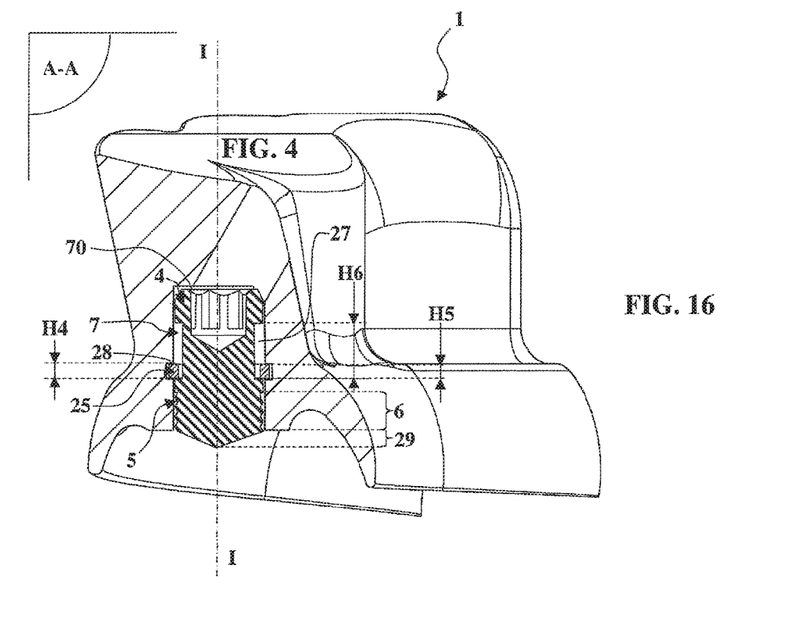
FIGS. 16 and 17 are sectional views of a second variant of the second embodiment of a transfixed multiple dental prosthesis.
Figure 17:
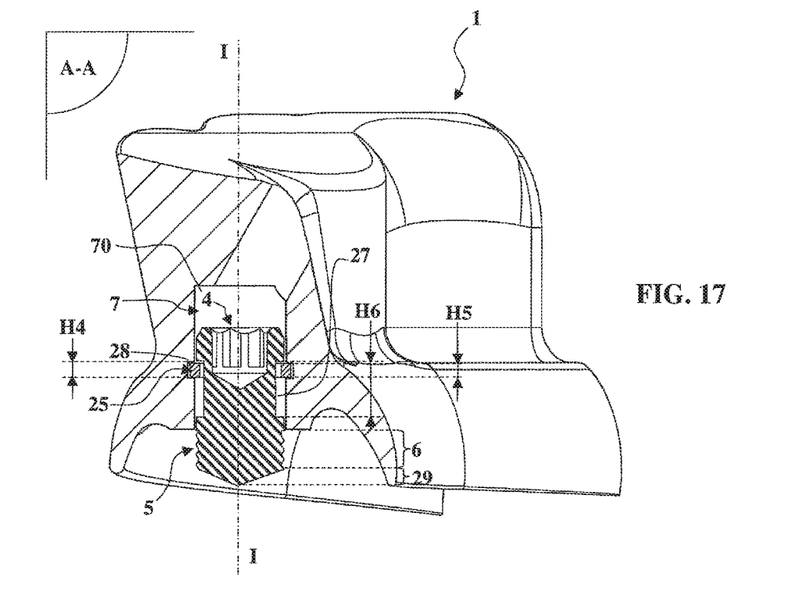

In the variant illustrated in FIGS. 16 and 17, this translational ability of the transfixing screw 4 to move between its retracted and screwing positions is afforded by the fact that the outer peripheral groove 27 formed on the transfixing screw 4 has a height H6, in the axial direction. I-I, greater than the height H5 of the retaining ring 25 engaging in the inner peripheral groove 28.

Figure 18:
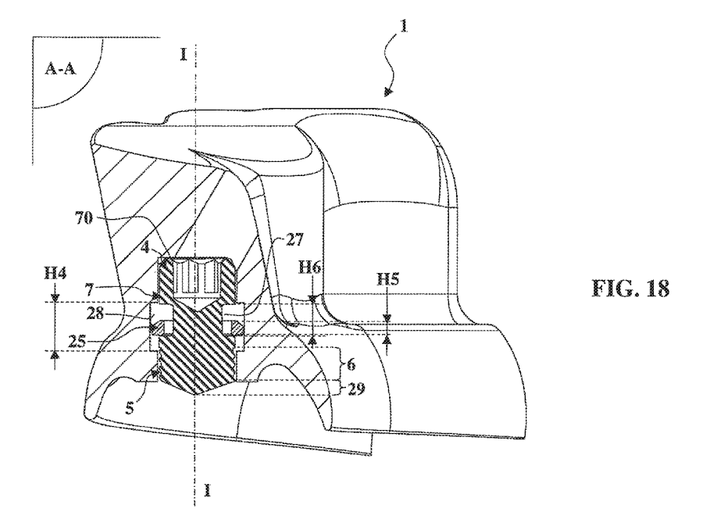
FIGS. 18 and 19 are sectional views of a third variant of the second embodiment of a transfixed multiple dental prosthesis.
Figure 19:
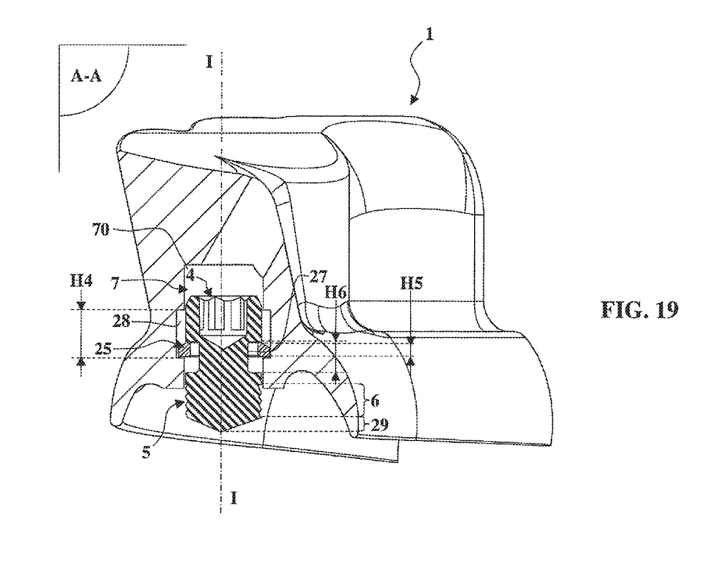

In the variant illustrated in FIGS. 1.8 and 19, the translational ability of the transfixing screw 4 to move between its retracted and screwing positions is afforded by the fact that the inner peripheral groove 28 and the outer peripheral groove 27 have respective heights H4 and H6, in the axial direction I-I, greater than the height H5 of the retaining ring 25 engaging in the inner peripheral groove 28.

In all of the embodiments illustrated in the figures, it will be seen that:

the shank 5 of the transfixing screw 4 terminates in a distal centering portion 29 following on from the threaded portion 6, the distal centering portion 29 has a cross section whose dimensions decrease in the direction away from the threaded portion 6.

In FIGS. 3, 14, 16 and 18, where the transfixing screw 4 is in the retracted position, it will be seen that the transfixing screw 4 protrudes from the bore 7, in which it is held captive, via all or part of its centering portion 29. Its threaded portion 5 does not protrude from the bore 7, in such a way as to keep it protected.

In FIGS. 14 to 19, the centering portion 29 is substantially conical, whereas it is substantially frustoconical in FIGS. 3, 4 and 11. Alternatively, a rounded shape can be used.

It will be seen more particularly from FIG. 11 that:

the threading 8 of the threaded portion 6 of the transfixing screw 4 has a first threading portion 61, and it has a second threading portion 62 following on from the first threading portion 61 and extending as far as the centering portion 29, the first threading portion 61 has a constant external diameter D1, the second threading portion 62 has an external diameter D2 which decreases progressively in the direction of the centering portion 29.

It will be seen from FIG. 12 that the threading 6 of the threaded portion 6 of the transfixing screw 4 has three threads 8a, 8b, 8c. The first internally threaded portion 12 of the implant 2 or 3 (FIG. 5) has a corresponding number of threads.

It is expressly indicated that the implant 2 or 3 of FIG. 5, with its first internally threaded portion 12 extending immediately from the orifice 11a of the inner bore 11, constitutes an independent invention for which patent protection will be able to be sought. Such a dental implant 2 or 3 can have a reduced overall length, limiting the risks of conflict with the transfixing screws of a transfixed dental prosthesis, all the more so since the arrangement of the first internally threaded portion 12 makes it possible to reduce the length of the transfixing screw.

In the first variant illustrated in FIGS. 5 and 6, the dental implant 2 or 3 is in one piece, and its upper end 2a or 3a is intended to pass at least in part through the mucosa.

Figure 20:
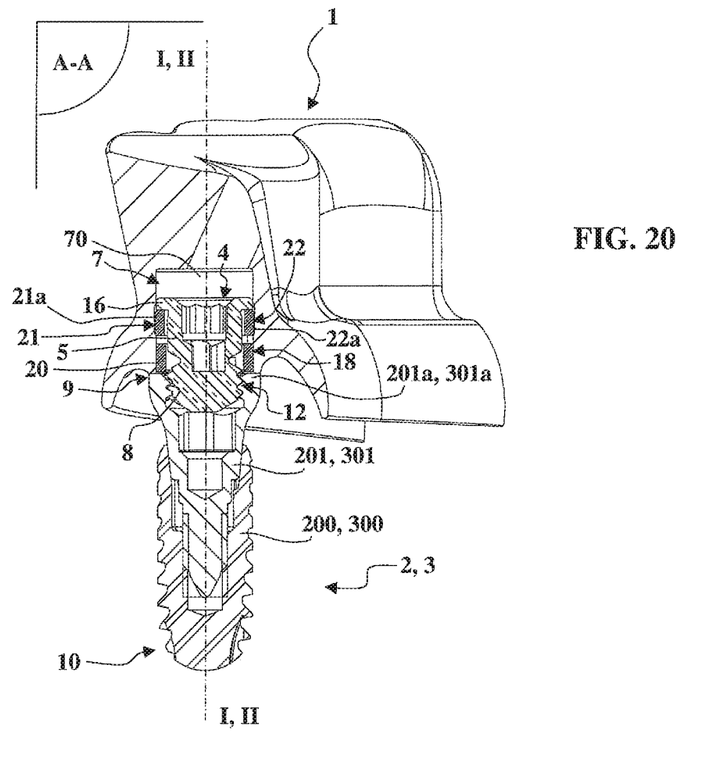
FIG. 20 is a sectional view of the transfixed multiple dental prosthesis of FIG. 1, on a section plane A-A illustrated in FIG. 2, attached and fixed to a second variant of an implant.

In a second variant illustrated in FIG. 20, the dental implant 2 or 3 is in two pieces, being composed of an osseous anchor 200 or 300 and a transmucosal extension 201 or 301. The transmucosal extension 201 or 301 has an upper end 201a or 301a intended to pass at least in part through the mucosa.

The present invention is not limited to the embodiments that have been explicitly described, and instead it includes the different variants and generalizations contained within the scope of the attached claims.

The invention claimed is:

1. Transfixed multiple dental prosthesis intended to be attached and fixed to a plurality of dental implants, said prosthesis including several transfixing screws, each having a shank with a threaded portion intended to be received by screwing in a respective dental implant, wherein:
    each transfixing screw is held captive in a respective bore formed in the transfixed multiple dental prosthesis, said respective bore extending along a respective axial direction,
    each captive transfixing screw is movable in rotation about the axial direction of the respective bore and is movable in translation along the axial direction of the respective bore between a retracted position and at least one screwing position,
    in the retracted position, the threading of the threaded portion of each transfixing screw does not protrude from the respective bore in which each transfixing screw is held captive,
    in the at least one screwing position, the threading of the threaded portion of the transfixing screw protrudes at least in part from the respective bore in which the transfixing screw is held captive.

2. Transfixed multiple dental prosthesis according to claim 1, wherein:
    the shank of each transfixing screw terminates in a distal centering portion following on from the threaded portion,
    the distal centering portion has a cross section whose dimensions decrease in the direction away from the threaded portion,
    in the retracted position, the centering portion of each transfixing screw protrudes from its respective bore.

3. Transfixed multiple dental prosthesis according to claim 2, wherein the centering portion is substantially conical or frustoconical.

4. Transfixed multiple dental prosthesis according to claim 2, wherein:
    the threading of the threaded portion of each transfixing screw has a first threading portion, and it has a second threading portion following on from the first threading portion and extending as far as the centering portion,
    the first threading portion has a constant external diameter,
    the second threading portion has an external diameter which decreases in the direction of the centering portion.

5. Transfixed multiple dental prosthesis according to claim 1, wherein the threading of the threaded portion of each transfixing screw has at least two threads.

6. Transfixed multiple dental prosthesis according to claim 1, wherein:
    each transfixing screw has a portion with a radial widening, from which there extends a transfixing screw portion that has an external cross section with dimensions smaller than those of the radial widening,
    each transfixing screw is held captive in its respective bore by way of a fixing member which simultaneously:
    engages at least in part in an inner peripheral seat formed in the respective bore of the transfixed multiple dental prosthesis,
    has, under the radial widening and around the transfixing screw portion, an external cross section with dimensions smaller than those of the radial widening.

7. Transfixed multiple dental prosthesis according to claim 6, wherein the inner peripheral seat formed in the respective bore, and/or the transfixing screw portion having an external cross section with dimensions smaller than those of the radial widening, have a height in the axial direction greater than the height of the part of the fixing member engaging in the inner peripheral seat, so as to allow the translation of the transfixing screw engaged in said respective bore between its retracted and screwing positions.

8. Transfixed multiple dental prosthesis according to claim 6, wherein:
    the fixing member is a retaining ring with a radial slit,
    the inner peripheral seat is an annular groove extending radially with respect to the axial direction of the bore.

9. Transfixed multiple dental prosthesis according to claim 6, wherein:
    the fixing member comprises an annular ring which has symmetry of revolution about a central axis and which extends along the central axis between a proximal end and a distal end,
    the fixing member comprises at least one angular portion developing in an arc between a first end, joined to the distal end of the annular ring, and a second free end,
    said at least one angular portion is in part movable from its first end, in a transverse plane perpendicular to the central axis, between a retracted position and at least one protruding position, being elastically returned permanently to the protruding position,
    in the retracted position, said at least one angular portion is included within the volume of a cylinder continuing the outer cylindrical surface of the annular ring, in the protruding position, the second free end of said at least one angular portion extends beyond the volume of the cylinder continuing the outer cylindrical surface of the annular ring.

10. Transfixed multiple dental prosthesis according to claim 9, wherein the inner peripheral seat has at least one angular groove portion extending radially with respect to the axial direction of the bore.

11. Transfixed multiple dental prosthesis according to claim 9, wherein the inner peripheral seat is an annular groove extending radially with respect to the axial direction of the bore.

12. Transfixed multiple dental prosthesis according to claim 1, wherein each transfixing screw is mounted rotatably and retained in translation in its respective bore by way of a compressible retaining ring, preferably by means of a radial slit, simultaneously engaging in an outer peripheral groove formed on said transfixing screw and in an inner peripheral groove formed in said respective bore.

13. Transfixed multiple dental prosthesis according to claim 12, wherein the inner peripheral groove formed in the respective bore, and/or the outer peripheral groove formed on each transfixing screw, have a height, in the axial direction, greater than the height of the retaining ring engaging in the inner peripheral groove formed in the respective bore, in such a way as to permit the translation of said transfixing screw between its retracted and screwing positions.

14. Dental assembly comprising:

a transfixed multiple dental prosthesis according to claim 1, a dental implant extending between a distal connection end, intended to receive the transfixed multiple dental prosthesis, and a proximal anchoring end, intended to be inserted in the maxillary or mandibular bone of a patient, comprising a blind inner bore that leads to the distal connection end, and comprising a first internally threaded portion intended to receive the threaded portion of a transfixing screw, wherein the first internally threaded portion extends from the orifice of the blind inner bore in the direction of the proximal anchoring end.

15. Dental assembly according to claim 14, wherein the dental implant has a screwing socket with a non-circular cross section, accessible from the orifice of the blind inner bore via the first internally threaded portion.

16. Dental assembly according to claim 14, wherein the dental implant has a second internally threaded portion, accessible from the orifice of the blind inner bore via the first internally threaded portion and the screwing socket, and having a threading diameter smaller than the threading diameter of the first internally threaded portion.

* * * * *